(12) United States Patent
Sarangapani et al.

(10) Patent No.: US 7,147,625 B2
(45) Date of Patent: Dec. 12, 2006

(54) LEG BAG ACCESSORY

(75) Inventors: Shantha Sarangapani, Walpole, MA (US); Fletcher Tifft Longley, Westwood, MA (US)

(73) Assignee: ICET, Inc., Norwood, MA (US)

( * ) Notice: Subject to any disclaimer, the term of this patent is extended or adjusted under 35 U.S.C. 154(b) by 588 days.

(21) Appl. No.: 10/611,301

(22) Filed: Jul. 1, 2003

(65) Prior Publication Data

US 2005/0004525 A1    Jan. 6, 2005

(51) Int. Cl.
*A61M 1/00* (2006.01)
(52) U.S. Cl. .................................. 604/317; 604/323
(58) Field of Classification Search ................ 604/540, 604/541, 544, 323, 333, 335, 523, 265, 317
See application file for complete search history.

(56) References Cited

U.S. PATENT DOCUMENTS

| | | | | |
|---|---|---|---|---|
| 3,396,727 A | * | 8/1968 | Mount ........................ 604/48 |
| 4,232,677 A | * | 11/1980 | Leibinsohn ................. 604/247 |
| 4,417,891 A | * | 11/1983 | Cianci ....................... 604/317 |
| 4,424,058 A | * | 1/1984 | Parsons et al. ............. 604/118 |
| 4,636,313 A | * | 1/1987 | Vaillancourt ................ 210/436 |
| 5,207,661 A | * | 5/1993 | Repschlager ................ 604/317 |
| 5,295,979 A | * | 3/1994 | DeLaurentis et al. ....... 604/265 |
| 5,300,049 A | * | 4/1994 | Hogan ....................... 604/317 |
| 5,429,620 A | * | 7/1995 | Davis ........................ 604/538 |
| 5,489,281 A | * | 2/1996 | Watanabe et al. ........... 604/317 |
| 5,616,138 A | * | 4/1997 | Propp ........................ 604/317 |
| 5,762,797 A | * | 6/1998 | Patrick et al. ............ 210/497.1 |
| 5,766,249 A | * | 6/1998 | Griffith ....................... 600/30 |
| 5,992,413 A | * | 11/1999 | Martin et al. ........... 128/201.13 |
| 6,540,806 B1 | * | 4/2003 | Reinhold ..................... 55/490 |
| 6,849,214 B1 | * | 2/2005 | Patil ........................ 264/45.1 |
| 2002/0030006 A1 | * | 3/2002 | Beck ........................ 210/411 |

* cited by examiner

*Primary Examiner*—Sharon Kennedy
(74) *Attorney, Agent, or Firm*—Richard D. Fuerle

(57) ABSTRACT

An accessory is connected between a leg bag and a urinary catheter to prevent microorganisms migrating from the leg bag up through the catheter. The accessory has a sleeve, connectors to connect the sleeve to the leg bag and to the urinary catheter, a filter positioned within the sleeve that can be coated with an antimicrobial composition, and a valve to prevent fluid from moving from the leg bag to the catheter. The antimicrobial coated sleeve can be used with or with out the filter. The filter is made by compounding a polymeric resin powder with an antimicrobial composition.

19 Claims, 8 Drawing Sheets

LEG BAG ACCESSORY

The invention reported here resulted from the work supported by the US National Institutes of Health Small Business Innovation Research (SBIR) Grant # 2R44 DK55891-022.

BACKGROUND OF THE INVENTION

This invention relates to a leg bag accessory that connects a Foley catheter to a leg bag. In particular, it relates to a leg bag accessory that contains an antimicrobial filter and a check valve.

Urinary drainage bag ("leg bags") attached to indwelling urinary catheters ("Foley catheters") are commonly used at hospitals and rehabilitation centers on long term and short term patients for incontinence after surgery, chronic disabilities, or other complications. The leg bags are frequently one of the three major sources for an ascending infection that cause urinary tract infections (UTI) in patients. (The other two points of entry are the catheter-leg bag connection and the catheter-skin junction). The leg bags become incubators for bacterial growth, most of which are pathogenic, such as *e. coli, p. mirabilis, pseudomonas, Candida*, and *staph*, and frequently antibiotic-resistant strains of those bacteria are present. While the leg bag is intended to keep contaminated urine from reentering the catheter, this nevertheless can occur and is one of the prime sources of UTI in patients.

Each year, more that 30 million urinary catheters are placed in patients in acute care hospitals and extended care facilities. Nosocomial (acquired at home or in nursing homes or hospitals) catheter-associated urinary tract infection (CAUTI) is the most common hospital-acquired infection in acute care hospitals, accounting for 40% of all nosocomial infections. (Stamm, W. E., "Catheter-associated urinary tract infections: Epidemiology, pathogenesis, and prevention," *Am J Med* 91 (suppl 3B): 65S–71S, (1991); Burke, J. P. and Riley, D. K., *Nosocomial urinary tract infection in hospital epidemiology and infection control.* Mayhall, C. G., editor. Baltimore: Williams and Wilkins (1996), pp. 139–153; Maki, D. G., Tambyah, P. A. "Engineering out the risk of infection with urinary catheters," *Emer Inf Dis* 7(2)1–5 (2001).) Nosocomial bacteriuria or candiduria develops in up to 25% of patients requiring a urinary catheter for at least 5 days, with a daily risk of 5%. (Stark, R. P. and Maki, D. G., "Bacteriuria in the catheterized patient," *N Engl J Med* 311:560–4 (1984)) Catheter-associated urinary tract infection is the second most common cause of nosocomial bloodstream infections. (Maki, D. G., "Nosocomial bacteremia. An epidemiologic overview" *Am J Med* 70:719–32 (1981); Krieger, J. N. et al., "Urinary tract etiology of bloodstream infections in hospitalized patients," *J Infect Dis* 148:57–62 (1983); Bryan, C. S. and Reynolds, K. L., "Hospital-acquired bacteremic urinary tract infection: epidemiology and outcome" *J Urol* 132:494–8 (1984)) Silent catheter-associated bacteriuria hosts an enormous reservoir of resistant organisms in the hospital which can be spread to other patients on the same units, particularly within ICUs (intensive care units). Studies by Platt and coworkers suggest that although most cases of catheter-associated bacteriuria are asymptomatic, CAUTI appears to be associated with significantly increased hospital mortality. (Platt, R. et al., "Mortality associated with nosocomial urinary tract infection." *N Engl J Med* 307(11):637–641 (1982))

Most microorganisms causing endemic CAUTI derive from the patient's own colonic and perineal flora Extraluminal infection may occur early (with in 24–48 hrs of cathetrization) by direct inoculation when the catheter is inserted, or by organisms ascending from the perineum by capillary action in the thin mucous film contiguous to the external catheter surface. (Tambyah, P. A. et al., "A prospective study of pathogenesis of catheter-associated urinary tract infections," *Mayo Clin Proc* 74(2): 131–6 (1999).) The intraluminal infection occurs after an average of five to six days from organisms growing in the leg bag reaching the catheter. Numerous strategies to prevent CAUTI have been examined in prospective trials, with the greatest success achieved by the use of sterile closed drainage systems. In a recent trial, use of a silver-hydrogel-coated catheter (Bardex® IC) to reduce the risk of extraluminally-acquired CAUTI was shown to reduce risk 25%, with no effect on the incidence of intraluminally-acquired CAUTIs, however. (Maki, D. G. et al., "A novel silver-hydrogel impregnated indwelling catheter reduces CAUTIs: a prospective double-blinded trial," Abstract, *Programs and Abstracts of the Society for Healthcare Epidemiology in America Annual Meeting*; Apr. 5–7 (1998) Orlando, Fla.)

Other measures, such as the daily application of antiseptic solutions or antiseptic ointment to the catheterized meatus or perineum and the addition of antiseptic solutions to the collection bag, have given disappointing results. Bacteria commonly gain access to the collection system. (leg bag) Once colonized, the leg bag becomes a reservoir for bacteria to multiply unchecked and causes infection when contaminated urine refluxes up the catheter into the patient's bladder. Such intraluminal contamination producing CAUTI occurs by a reflux of microorganisms gaining access to the catheter or from failure of closed drainage or by the slow migration of the microorganisms, mostly gram negative from the leg bag to the catheter and to the bladder eventually and accounts for about one-half of CAUTIs.

SUMMARY OF THE INVENTION

Currently, the leg bag or bed bag collection systems are connected by a simple tube of varying length to the catheter. The leg bag accessory of this invention is positioned between the collection system and the catheter, replacing the tube partially or fully. The accessory prevents the reflux of contaminated urine from the leg bag through the catheter into the bladder. The accessory employs a check valve to prevent the reflux of urine and an antimicrobial filter to impede the movement of microorganisms from the collection system to the catheter, inhibit their growth, and kill them. The accessory provides a better quality of care to the patient.

Since an average amount of $39,000 per year per patient is currently spent in treating catheter-related infections and complications, the use of the accessory of this invention will significantly reduce hospital costs.

The accessory is inexpensive, easy to use, and contains only biocompatible materials. It is an add-on to the collection system and the clinician can either use it or remove it if it is not needed.

It is therefore a principal object of the present invention to provide a leg bag accessory that prevents or limits ascending infections between leg bags and the catheterized patient.

DESCRIPTION OF THE PREFERRED EMBODIMENTS

Figure 1:
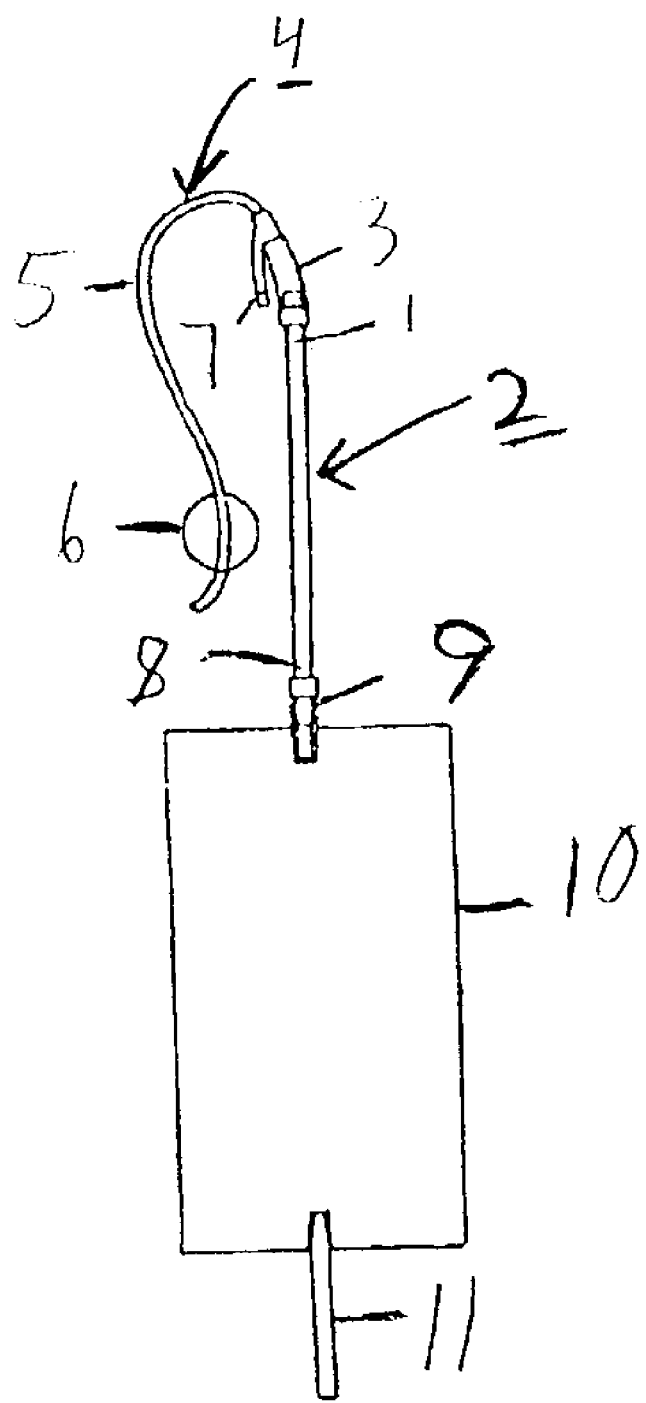
FIG. 1 is a side view of a certain presently preferred embodiment of a leg bag accessory according to the present invention mounted between a Foley catheter and a leg bag.

Referring to FIG. 1, the upper end 1 of leg bag accessory 2 is connected by universal connector 3 to urinary catheter 4. To prevent catheter 4 from becoming dislodged, catheter 4 has a tube 5 having a balloon 6 which is inflated by injecting sterile water into catheter 4 at inlet 7 after catheter 4 has been inserted into a bladder.

At the lower end 8 of accessory 2 is another universal connector 9, which connects accessory 2 to collection leg bag 10. Urine can be emptied from leg bag 10 through drain 11.

Figure 2:
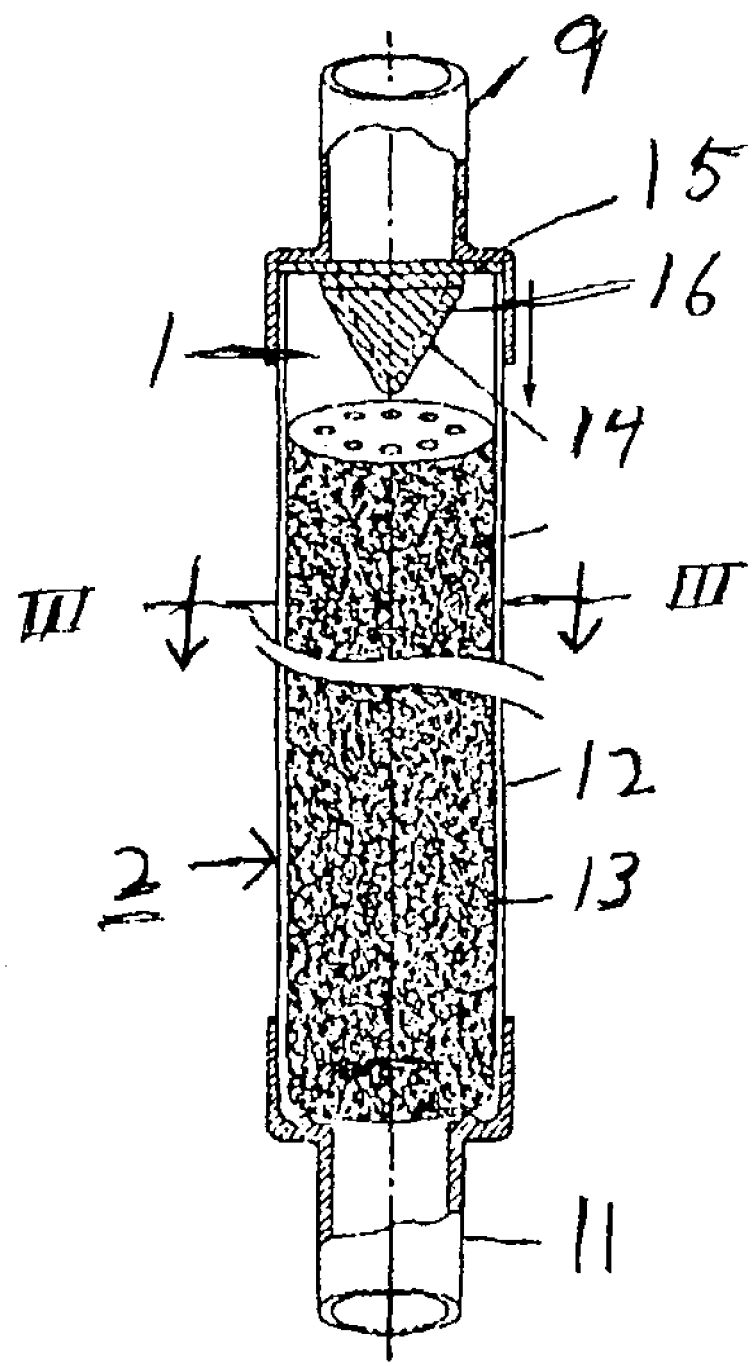
FIG. 2 is a partially cut-away perspective view of the leg bag accessory shown in FIG. 1.
Figure 3:
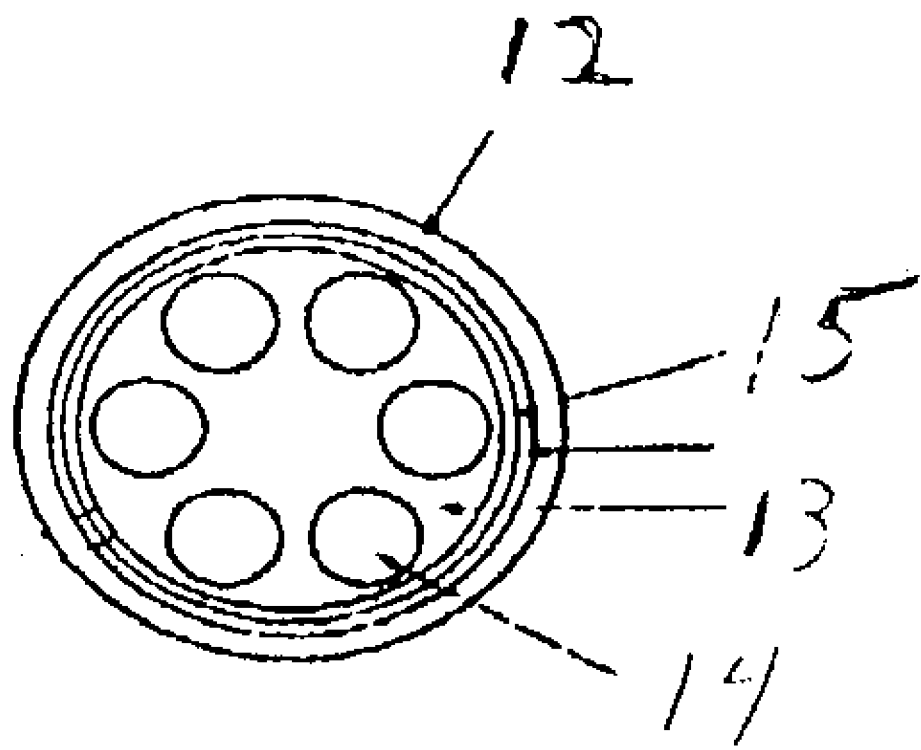
FIG. 3 is a cross sectional view taken through III—III in FIG. 2.
Figure 4:
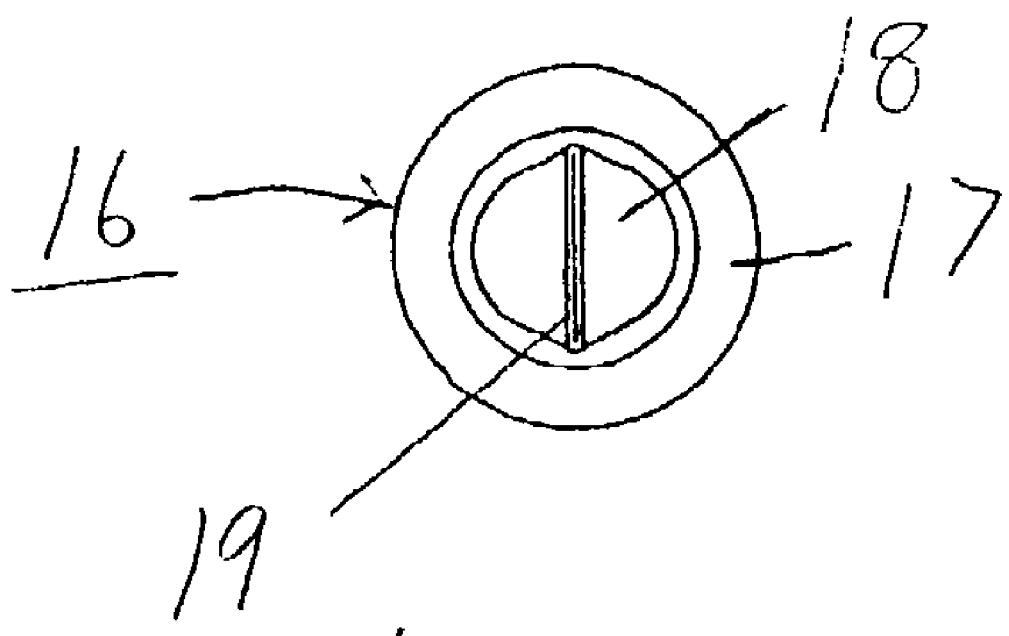
FIG. 4 is an inverted plan view of the reflux check valve shown in FIG. 1.

Referring now also to FIGS. 2 to 4, accessory 2 comprises tubular sleeve 12 that encloses filter 13 having six passageways 14 therethrough. Filter 13 is preferably an open-pore, sponge-like material, so that urine can pass through filter 13 as well as around it. Sleeve 12 is preferably thermally welded, rather than glued, to connectors 9 and 11 so that the connections will be leak-free over the entire life of the accessory. The inside surface of sleeve 12 is preferably covered with antimicrobial coating 15.

Referring particularly to FIG. 4, check valve 16 has a flat portion 17 that sits on top of sleeve 12 and a duck-bill portion 18. Duck bill portion 18 has a narrow slit 19 at its base which permits urine to pass downward into accessory 2, but inhibits the movement of urine upward into catheter 4. While FIG. 4 shows a duck bill anti-reflux valve, other types of check valves can also be used, such as a ball in a chamber, or a flap over an aperture.

Sleeve 12 is preferably made of a flexible, transparent plastic such as silicone, polyethylene, polypropylene, polyurethane, or polycarbonate, but it could also be made of other materials, such as latex or polyvinylchloride; the preferred material is silicone because of its well-accepted biocompatibility. Sleeve 12 is preferably cylindrical, but could also have other shapes, such a rectangular. Sleeve 12 can be manufactured in various sizes to accommodate different patients. It may be, for example, about 2 to about 36 inches long and may have a diameter of about 0.2 to about 1 inch. Preferably, it has a length is about 2 to about 15 inches and a diameter of about 0.3 to about 0.7 inches.

A typical formula for antimicrobial coating 15 for a silicone sleeve can be made by diluting about 10 to about 30 wt % of an antimicrobial composition, such as the one used in Example 1, with a hexane solution of RTV (room temperature vulcanization) silicones (GE Plastics). The mixture can be dip-coated or spray-coated onto the inner surface of the sleeve and dried at about 70° C. overnight. For other plastics, medically approved polyurethanes such as Tecoflex (medical grade polyurethane) or Hypol ((a polyurethane prepolymer adhesive (Dow chemicals) or Polyvinyl chloride (PVC) can be dissolved in a solvent such as tetrahydrofuran or acetone. An antimicrobial composition is blended into the polyurethanes or silicones and the mixture can be coated on the inside of the sleeve as described above. Such coated sleeve lengths range from 0.1" to 36" inches.

Figure 5:
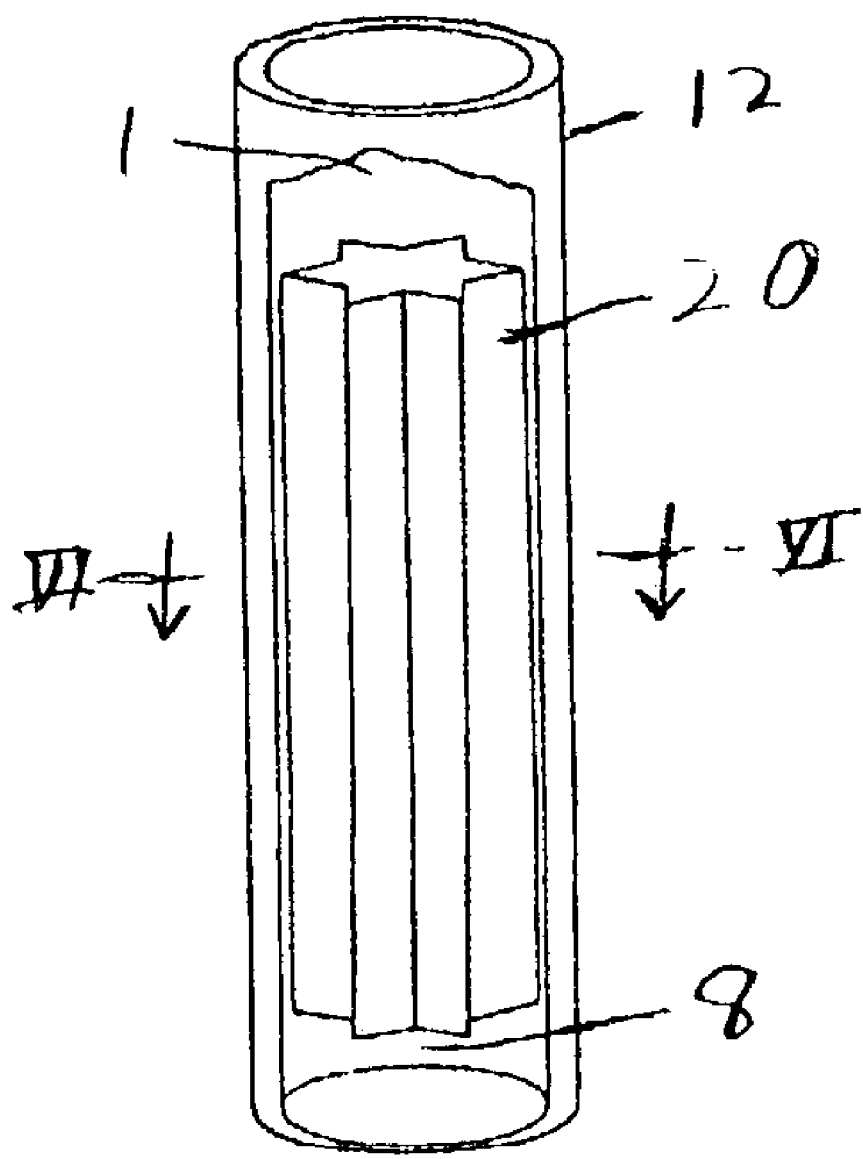
FIG. 5 is a partially cut-away perspective view of a portion of another embodiment of a leg bag accessory according to this invention.
Figure 6:
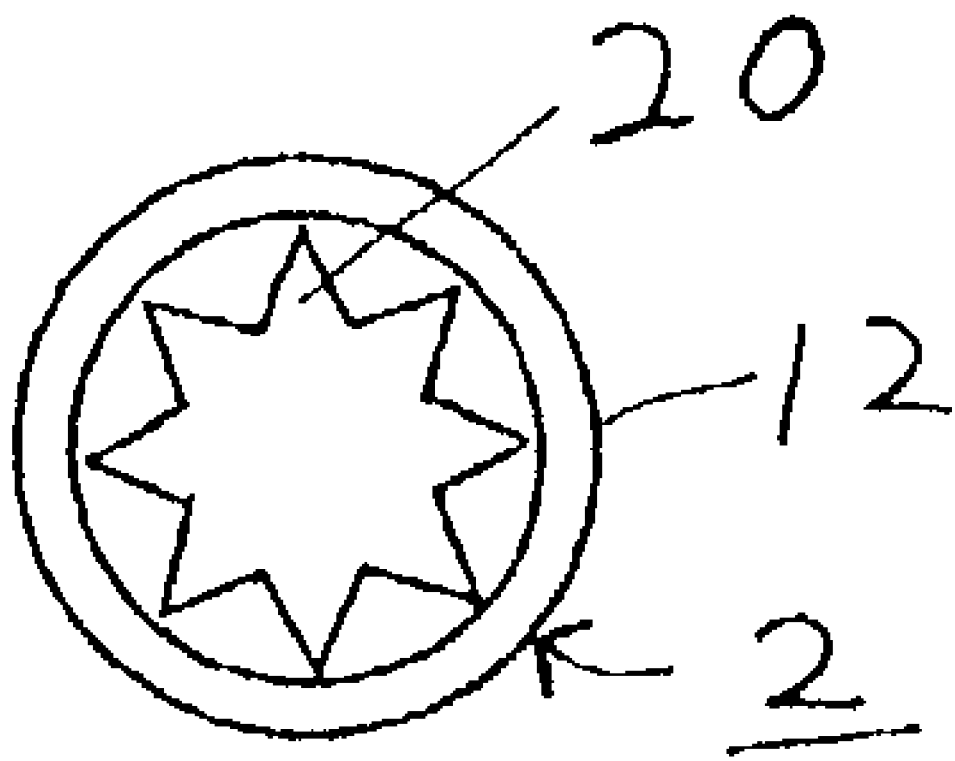
FIG. 6 is a cross-sectional view through VI—VI in FIG. 5.

Referring now to FIGS. 5 and 6, an alternative star-shaped filter 20 is shown. Other filter configurations can also be used such as a multilumen configuration (a bundle of stacked tubes), a corrugated configuration (folded sheets), or a rolled configuration (a rolled up sheet). The filter configuration is preferably selected so that urine flow is not occluded should sleeve 12 be severely flexed. In addition, the configuration of filter 13 should be selected so that there is no passage past filter 13 that is outside the zone of inhibition.

The "zone of inhibition" is the distance from filter 13 in which bacteria are killed or inhibited from growing due to leaching of antimicrobial material from filter 13. That is, filter 13 contains an antimicrobial material and is made to leach that antimicrobial material into urine passing through or around it. This antimicrobial material kills or inhibits the growth of any bacteria that are within the zone of inhibition, which is typically about 1 to about 3 mm from the surface of filter 13. The zone of inhibition is increased if more or more potent antimicrobial material is used, if more antimicrobial material leaches into the urine, or if the urine flow is slow; other factors may also affect the zone of inhibition.

Filter 13 is preferably biocompatible so that, in the very unlikely event that some of it finds its way up through the catheter into the bladder, it will not be harmful to the patient. Also, filter 13 preferably does not contain an antibiotic because that could promote the development of antibiotic-resistant bacteria.

The filter material is preferably made by compounding (i.e., heating at a temperature of about 160 to about 190° F.) a well-dispersed mixture of about 60 to about 90 wt % of a resin and about 10 to about 40 wt % of a antimicrobial composition. The filter material is preferably about 70 to about 80 wt % resin and about 20 to about 30 wt % antimicrobial composition. More resin is undesirable because it would dilute the antimicrobial material and less resin is undesirable because the mechanical properties of the filter may be compromised. Examples of suitable resins include sytrene-butadiene rubbers, polyurethanes, silicone-polyurethanes, polyvinylchloride, polyolefin elastomers, and silicone. Materials such as inorganic/organic hybrid materials, carbon and other high area filled materials, such as nanocomposites, hydrogels such as polyoxazoline, polyvinylalcohol, polyhydroxy acrylates, super absorbent polymers, and biodegradable and natural polymeric materials such as cellulose or sponges, can also be used as carriers for the antimicrobial composition. The preferred resins are polyurethane sold by Thermedics (MA) or a styrene-butadiene hybrid sold as Teknor, (Apex Teknor, RI) or Kraton sold by GLS Corp (IL) a distributor for Shell chemicals. The resin particles can have a diameter of about 0.01 to about 3 mm (measured as if spherical); particle sizes less than about 0.01 mm are hard to obtain and particle sizes greater than about 3 mm are less desirable because they have less surface area; a particle size of about 2 to about 3 mm is preferred.

The antimicrobial composition preferably contains four components:
  (1) antimicrobial material;
  (2) calcium chelator;
  (3) pigment; and
  (4) lubricant.

The purpose of the antimicrobial material is to kill bacteria, yeasts, and molds. Examples of suitable antimicrobial materials include nanosize particles of metallic silver or silver containing about 2.5 wt % copper, salts such as silver citrate, silver acetate, silver benzoate, bismuth pyrithione, zinc pyrithione, sodium pyrithione, bismuth salts, various food preservatives such as methyl, ethyl, propyl, butyl, and octyl benzoic acid esters (generally referred to as parabens), citric acid. Silver particles having a particle size of about 1 to about 100 nm are believed to slowly release silver ions, Ag+, which are antimicrobial. Silver citrate is the preferred antimicrobial material because it is a very effective and safe bactericide due to the rapid release of silver ions. Butyl paraben and octyl paraben are the preferred antimicrobial materials for yeasts and molds due to their low solubility in water. About 60 to about 100 wt % of the antimicrobial composition can be the antimicrobial material; less is ineffective. Preferably, about 35 to about 50 wt % of the antimicrobial material is used. The antimicrobial material slowly leaches from the filter, keeping the zone of inhibition free of live bacteria, yeasts, and molds.

The chelator prevents deposits of calcium and/or magnesium from forming, which may impede the flow of urine. Examples of suitable chelators include EDTA, citric acid, hydroxyethylidene phosphonic acid, polyvinylphosphonic acid, polyvinylsulfonate, acrylic acid, and aminophosphonic acid. The preferred chelator is citric acid because of its ability to solubilize silver and form complexes with calcium ions. Zero to about 25 wt % (based on the weight of the antimicrobial composition) can be chelator. More is undesirable because of its acidity and less is undesirable because the efficacy of the long term release is reduced. Preferably, about 20 to about 30 wt % of the chelator is used.

The purpose of the pigment is for coloring, as the silver imparts a dark greyish color. The addition of the pigment imparts a bluish grey shade. Copper phthalocyanine (pigment blue) is the preferred pigment because it is believed to also have a bacteriostatic effect and is used in surgical sutures. Zero to about 0.25 wt % (based on the weight of the antimicrobial composition) can be pigment. More is undesirable because of the high intensity in color and the blocking effect of the large pigment molecules and less is undesirable because the benefit of the color is lost (i.e., the color is visually not pleasing). Preferably, about 0.005 to about 0.01 wt % of the pigment is used.

The purpose of the lubricant is to make the surface lubricious, when contacted by aqueous fluids, such as urine which is advantageous because it helps to prevent bacteria from adhering to the filter. Examples of suitable lubricants include polyethylene oxide, polyacrylic acid, polyvinylpyrrolidone, polyvinyl alcohol, and derivatives thereof. The preferred lubricant is polyethylene oxide because it discourages cell adhesion and can be incorporated into the antimicrobial composition. Zero to about 3 wt % (based on the weight of the antimicrobial composition) can be lubricant. More is undesirable because of processing issues and less is undesirable because the surface is less lubricious. Preferably, about 2 to about 3 wt % of the lubricant is used.

A preferred antimicrobial composition is about 10 to about 25 wt % silver citrate, about 5 to about 10 wt % nanosize (i.e., less than about ten nanometers) silver powder, about 5 to about 10 wt % EDTA or a vinyl phosphonic acid or hydroxy ethyl phosphonic acid, about 20 to about 40 wt % butyl paraben, about 10 to about 25 wt % citric acid about 10 to about 15 wt % hydroxyethylidene phosphonic acid, and about 2 to about 3 wt % polyethylene oxide. Other examples of suitable antimicrobial compositions are described in U.S. Pat. Nos. 5,328,954 and 5,877,243, the teachings of which are incorporated herein by reference.

To make the filter, the mixture of the resin and the antimicrobial composition can be extruded at about 100 to about 200° F. using the special die that forms the filter in the desired configuration. The filter can also be formed by molding or shaping the mixture of the resin and the antimicrobial composition.

EXAMPLE 1

This example illustrates the ability of the accessory of this invention to protect a catheterized bladder from infection by blocking the ascending migration of bacteria from a contaminated leg bag. An in vitro model was used.

A antimicrobial composition was prepared of 7 wt % nanosize silver particles (from Nanopowder Industries, Israel), 18 wt % silver citrate (Aldrich), 36 wt % butyl parabens (Sigma Aldrich), 34 wt % citric acid (Sigma Aldrich), 0.25 wt % copper phthalocyanine (Aldrich, Minn.), 1.75 wt % polyethylene oxide (MW=100,000), and 3 wt % EDTA. The antimicrobial composition was blended as a fine powder and 68 gms of the powder was mixed with 386 gms of resin and pellets were formed by extruding at 180° F. The pellets were then extruded through an 7 lumen die at 170 to 200° F. to form the filter material. The filter material was packed into 4 inch long silicone tubes 0.5 inches in diameter which were connected to leg bags and catheters. The control accessories contained the same length of silicone tube connector and a filter made with the same resin, but with no antimicrobial composition in it.

A simple physical model of the catheterized bladder and a drainage system was used with the leg bag accessory located between the base of the catheter and the leg bag inlet. Synthetic urine containing tryptic soy broth (TSB) was supplied to the model at 0.5 mL/minute and the leg bag was contaminated with *Escherichia coli* and *Proteus mirabilis* strains isolated from UTI patients and leg bags, respectively. Over 10 to 15 days, urine from the leg bag accessory and the base of the catheter were examined for contamination.

Figure 7:
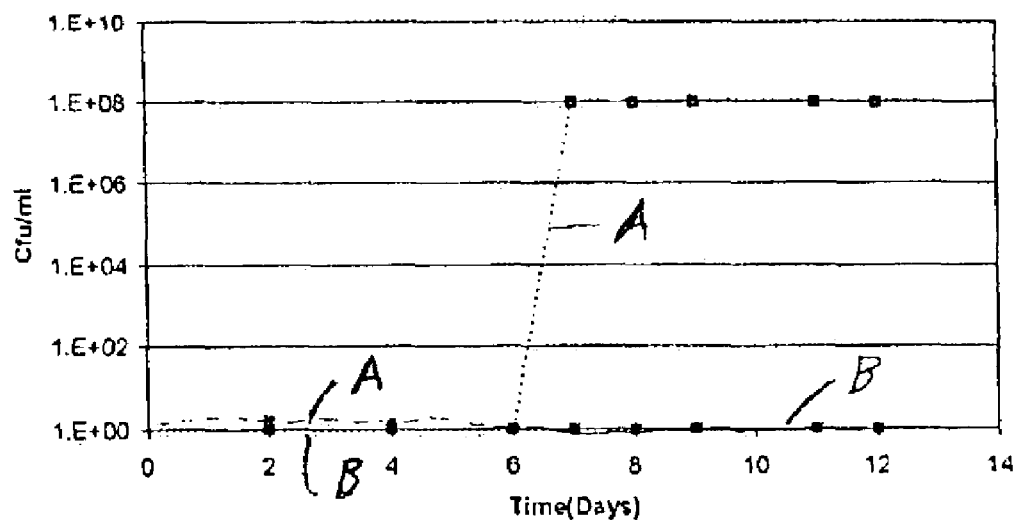
FIG. 7 is a graph showing the results of an in vitro study of a catheterized bladder mode with and without the using the accessory of this invention.

Bacteriological analysis showed that the mean time for the bacteria to reach the catheter base for three separate studies ranged from 3 days to 8 days for the control leg bag accessories. Urine from the catheter bases of the leg bag accessories with the accessories remained sterile for over 14 days, when the reactor was stopped, as shown in Table I and FIG. 7. These "in vitro" tests suggest a useful role for the accessory in controlling infection in patients undergoing short and long term in-dwelling catheterization.

TABLE I

| RUN | SAMPLING SITES | Antimicrobial Material | | Control | | CHI SQUARE P VALUES |
|---|---|---|---|---|---|---|
| | | Total No. of Samples | % with Growth | Total No. of Samples | % with Growth | |
| 5 | Catheter Base | 15 | 0.0% | 15 | 73.3% | p < 0.0001 |
| 6 | Leg Bag Only | 18 | 53.8% | 18 | 100% | p = 0.005 |

TABLE I-continued

| RUN | SAMPLING SITES | Antimicrobial Material | | Control | | CHI SQUARE P VALUES |
|---|---|---|---|---|---|---|
| | | Total No. of Samples | % with Growth | Total No. of Samples | % with Growth | |
| 7 | Catheter base | 16 | 0.0% | 15 | 73.3% | p = 0.0003 |
| 8 | Tube Bottom* | 10 | 0.0% | 12 | 58.3% | p = 0.020 |

*Part of the same connecting tube that is proximal to the leg bag inlet.

The leachates from the antimicrobial leg bag accessory did not prevent the growth of the organisms in the leg bags. However, visible discoloration and heavy encrustation were absent in the test leg bag systems compared to the control systems. Scanning electron microscopy showed extensive biofilms on the control leg bag accessories. Typically, a lawn growth was observed when samples from silicon sleeves from control leg bag accessories were cultured but the corresponding silicone sleeves from leg bag accessories according to this invention did not show any biofilms or any viable cells.

EXAMPLE 2

This example illustrates the performance of the antimicrobial filter material when subjected to continuous daily challenge of bacteria in human urine medium as well as in synthetic urine containing a rich broth called Brain Heart Infusion Broth (BHIB) or TSB (Tryptic soy broth) that facilitates the growth of bacteria.

In this example, one inch long samples of the antimicrobial filter material prepared in Example 1 were cut, weighed, and placed in two culture tubes with 0.5 mL of filter-sterilized human urine (HU) or synthetic urine or synthetic urine (SU) containing BHIB. The urine was inoculated each with 1000 cfu/ml (colony forming units per ml) of three pathogens isolated from patients. (VA hospital-*E. coli* Hu734, a *P. mirabilis* strain, and *Staphylococcus aureus*). A tube containing only 0.5 ml of urine was prepared as a control and the organisms were inoculated. Each day samples were removed from the tubes, the media was replaced, and the samples were rechallenged. Aliquots were plated to quantify the bacterial growth. Table II shows the efficacy of the antimicrobial filter material. In the table, "SU" is synthetic urine and "BHIB" is brain heart infusion broth.

TABLE II

Results of the continuous challenge tests.

| Run | Microorganism Approx: 1000 cells each | Media | With antimicrobial Composition | | Control Total No. | | CHI SQUARE P Values |
|---|---|---|---|---|---|---|---|
| | | | Total No. of Challenges | % with Growth | of Challenges | % with Growth | |
| 1 | *E. coli* + *P. mirabilis* | 90 wt % SU + 10 wt % BHIB | 39 | 23.1% | 13 | 84.6% | <0.0001 |
| 2 | *E. coli* + *P. mirabilis* | 90 wt % SU and 10 wt % TSB | 46 | 4.3% | 21 | 90.4% | <0.0001 |
| 3 | *E. coli* | 90 wt % SU + 10 wt % TSB | 19 | 5.3% | 18 | 100% | <0.0001 |
| 4 | *E. coli* + *P. mirabilis* | HU | 32 | 3.2% | 16 | 81.3% | <0.0001 |
| 5 | *S. aureus* | HU | 24 | 0.0% | 12 | 83.3% | <0.0001 |

The results were analyzed by comparing the percent of samples that were found to be non-sterile for the antimicrobial filter material vs. the control filter material. In this situation, the most straightforward comparison is simply 2×2 contingency tables using the number of samples in each category: antimicrobial filter material vs. control filter material for sterile vs. non-sterile samples using all the samples as random tests. The data was then analyzed by Chi-square testing (or Fisher Exact for small numbers) with the null hypothesis that there is no difference between the adjusted categories. As can be seen in Table II, the differences are highly significant.

EXAMPLE 3

This example illustrates the longevity of the antimicrobial action of the filter material when washed extensively with synthetic urine, simulating the daily urine flow output of about 1 L/day.

Figure 8:
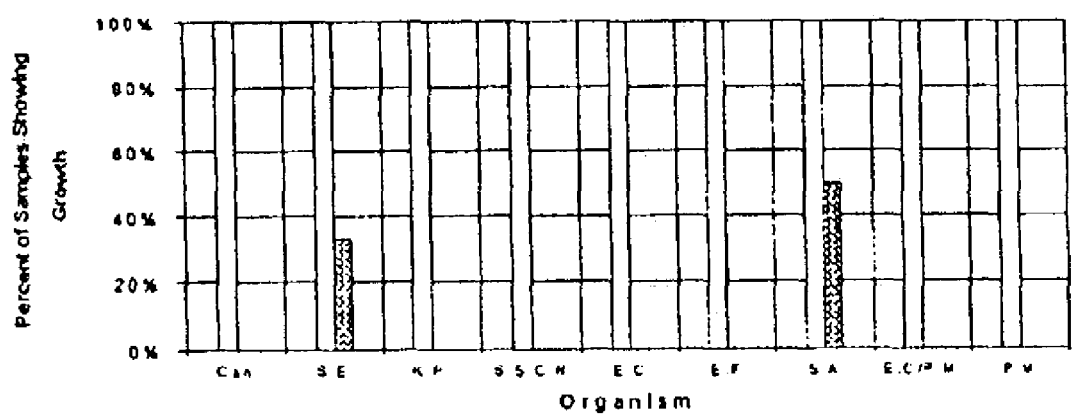
FIG. 8 is a graph showing the efficacy of the antimicrobial material from this invention after extensive washing in synthetic urine.

In long term wash and challenge studies, about 30 2-inch long pieces of the antimicrobial material of Example 1 and 30 2-inch long pieces of the control silicone were suspended and washed by gentle stirring in 1 L of filter sterilized simulated urine solution containing 1% TSB in a 1 L bottle. Both the controls and the antimicrobial material were suspended in the same bottle with change of solution every 24 hours. Duplicate samples at various time points were subjected to challenge by inoculation of clinical strains followed by incubation in real human urine. The clinical strains resistant to certain antibiotics tested were *S. aureus*, (SA), *S.* epidermidis, (SE), Coagulase negative Staph aureus (CN), Pseudomonas aeruginosa, Klebsiella pneumoniae, (KP), Vancomycin resistant enterococcus (EF), E. coli (EC), Candida (Can), and Proteus mirabilis (PM). These strains were isolated from venous and urinary catheters and blood culture bottles supplied by the VA Hospital in W. Roxbury, Mass. When tested by challenging them with high number of microorganisms, the results shown in FIG. 8 were obtained. Note the significant absence of microbial growth in the presence of the antimicrobial material. Where growth was noted in some samples, it was less than 100 colonies compared to confluent lawns in the controls. The results, shown in FIG. 8, illustrate the consistent efficacy of the antimicrobial material in inhibiting bacterial growth for up to 21 days.

EXAMPLE 4

This example illustrates the antimicrobial release characteristics of the antimicrobial material from Example 1. A sample of the filter material from Example 1 was consecutively extracted on a daily basis with filtered human urine or PBS under USP conditions (4 gms/20 ml) at 37° C. for 24 hrs. The resulting solutions were analyzed for silver and paraben content. The results are given in the following table (Table III)

TABLE III

Daily concentrations of silver and paraben released from the antimicrobial material.

| Extraction medium | Butyl Paraben | | Silver | |
|---|---|---|---|---|
| | HU | PBS | HU | PBS |
| Day 1 | 190 ppm | 159 | 11 ppm | 0.78 |
| Day 2 | 341 | 166 | 11 | 1.0 |
| Day 3 | 220 | 185 | 9 | 0.41 |
| Day 4 | 404 | 177 | 7 | 0.4 |
| Day 5 | 200 | 173 | 6 | 0.4 |
| Day 6 | | 166 | | 0.41 |
| Day 7 | | 180 | | 0.39 |

The above table shows there is a near steady release of the components from the antimicrobial filter. The HU extracted ten times more than PBS. Since 1 ppm of silver is biocidal, the concentrations near the surface of the antimicrobial device were high enough to prevent the migration of microorganisms past the filter.

EXAMPLE 5

Three leg bag accessories 8 inches long by 0.5 inches in diameter, fitted with "duck bill" anti-reflux check valves, as shown in FIGS. 2 and 4, were tested. Water was slowly pumped into the outlet of each accessory up to the check valve. Pressure was controlled by splitting the pump outlet, with one part going to check valve and the other part going to a needle valve and recycling to the pump reservoir. The pressure was increased in increments of 2 psi from a pressure of 2 psi to a pressure of 20 psi, holding at each pressure for 5 minutes. None of the valves failed in the three accessories tested. The procedure was repeated in increments from 11 to 14 psi up to 27 to 30 psi. One valve inverted at 27 to 30 psi, which is a much greater pressure than the valve would normally be subjected to.

An aqueous solution of 0.02 M NaCl was pumped into the inlets of the accessories to determine the resistance of the check valve to the flow of the solution pass it. The test was conducted with a leg bag and a catheter properly attached and a pressure gage at the inlet. The reading of the pressure gage was at noise level and could be considered to be zero.

To give a more precise reading at low pressures, a U-tube filled with water was connected in between the pump and the catheter. The saline solution was pumped pass the U-tube at a rate of 1 ml/min. There was no pressure increase from the flow of the saline solution into the accessory. When the pumping was stopped, the solution in the U-tube immediately drained into the accessory due to a siphon effect.

While the foregoing invention has been described with respect to its preferred embodiments, various alterations and modifications may occur to those skilled in the art. All such alterations and modifications are intended to fall within the scope of the appended claims.

We claim:

1. An accessory for connecting in between a urinary catheter and a leg bag comprising
   (A) a sleeve having an upper end and a lower end;
   (B) connectors for connecting the upper end of said sleeve to said urinary catheter and the lower end of said sleeve to said leg bag;
   (C) a filter within said sleeve that comprises about 70 to about 90 wt % compounded polymeric resin and about 10 to about 30 wt % antimicrobial composition; and
   (D) a valve within said sleeve at said upper end for impeding the flow of fluid from said accessory into said urinary catheter.

2. An accessory according to claim 1 wherein said sleeve is a natural rubber or a synthetic polymer.

3. An accessory according to claim 2 wherein said sleeve is a continuous part of the leg bag or the catheter.

4. An accessory according to claim 1 wherein said sleeve is about 0.1 to about 36 inches long and about 0.2 to about 1 inch in diameter.

5. An accessory according to claim 1 wherein the inside surface of said sleeve is coated with an antimicrobial coating.

6. An accessory according to claim 1 wherein said connectors are thermally welded or adhesively bonded to said sleeve.

7. An accessory according to claim 1 wherein said filter is extruded.

8. An accessory according to claim 1 wherein said filter is a bundle of separate tubes.

9. An accessory according to claim 1 wherein said filter has a star-shaped configuration.

10. An accessory according to claim 1 wherein said filter has a multiluminal configuration.

11. An accessory according to claim 1 wherein said filter has a folded configuration.

12. An accessory according to claim 1 wherein said valve occupies a space above said filter.

13. An accessory according to claim 1 wherein said polymeric resin is selected from the group consisting of polyurethanes, polyurethane sponges, styrene-butadiene based polymers, their blends or copolymers or derivatives, and silicone, or blends or and its copolymers.

14. An accessory according to claim 1 wherein said polymeric resin has a particle size of about 0.01 to about 3 mm in diameter.

15. An accessory according to claim 1 wherein said polymeric resin is selected from a group comprising common plastics, polymer resins, including inorganic/organic hybrid materials, carbon and other high area filled materials such as nanocomposites, superabsorbent polymers, hydrogels, biodegradable and natural polymeric materials such as cellulose or sponges and synthetic sponges.

16. An accessory according to claim 1 wherein said antimicrobial composition comprises
 (A) about 60 to about 100 wt % of an antimicrobial material;
 (B) 0 to about 25 wt % of a calcium chelator;
 (C) 0 to about 0.25 wt % of a pigment; and
 (D) 0 to about 3 wt % of a lubricant.

17. An accessory according to claim 1 wherein said antimicrobial composition comprises
 (A) about 30 to about 60 wt % of a bactericide selected from the group consisting nanosize particles of silver, nanosize particles of silver with 2.5 wt % copper, silver citrate, silver acetate, silver benzoate, bismuth salicylate, bismuth pyrithione, zinc pyrithione, bismuth salts, parabenzoic acid ester, citric acid, sodium pyrithione, and mixtures thereof;
 (B) about 20 to about 30 wt % of a calcium, chelator selected from the group consisting of ethylene diamine tetra acetic acid, citric acid, hydroxyethylidene phosphonic acid, polyvinylphosphonic acid, polyvinylsulfonate, poly acrylic acid, aminophosphonic acids, and mixtures thereof;
 (D) about 0.005 to about 0.01 wt % copper phthalocyanine; and
 (E) about 2 to about 3 wt % of a lubricant selected from the group consisting of polyethylene oxide, polyvinylpyrrolidone, polyacrylic acid polyvinyl alcohol, and derivatives and mixtures thereof.

18. An accessory for connecting a leg bag to a urinary catheter comprising
 (A) a flexible plastic sleeve having an upper end and a lower end;
 (B) plastic connectors for connecting the upper end of said sleeve to said urinary catheter and the lower end of said sleeve to said leg bag;
 (C) a filter within said sleeve having a zone of inhibition that includes all passages therethrough and therearound, where said filter comprises a compounded mixture of
  (1) about 60 to about 90 wt % polymeric resin powder; and
  (2) about 10 to about 40 wt % of a antimicrobial composition that comprises
   (a) about 35–67% of an antimicrobial for bacteria and fungi;
   (b) about 14 to about 29 wt % of a calcium chelator;
   (C) about 0.05 to about 0.1 wt % of a pigment; and
   (d) about 2 to about 3 wt % of a lubricant; and
  (D) a valve within said sleeve at said upper end for impeding the flow of fluid out of said accessory and into said urinary catheter.

19. An accessory for connecting in between a leg bag and a urinary catheter comprising
 (A) a plastic sleeve having an upper end and a lower end;
 (B) a first plastic connector thermally welded to the upper end of said sleeve for connecting said sleeve to said urinary catheter and a second plastic connector thermally welded to the lower end of said sleeve for connecting said sleeve to said leg bag;
 (C) a filter occupying the space within said sleeve except near said upper end of said sleeve and having a zone of inhibition that includes all passages therethrough and therearound, where said filter comprises an extruded, molded, or shaped material that comprises
  (1) about 70 to about 90 wt % polymeric resin powder selected from the group consisting of styrene-butadiene hybrids, polyurethanes, copolymers and hybrids thereof, silicones and hybrids, cellulose powder, hydrogels such as polyacrylates, polyoxazoline, alginates, p-hema, (polyhydroxy ethyl acrylate) polyvinylalcohol and its copolymers, and mixtures thereof; and
  (2) about 10 to about 30 wt % a antimicrobial composition that comprises
   (a) about 10 to about 25 wt % silver citrate;
   (b) about 5 to about 8 wt % nanosilver containing about 2.5 wt % copper;
   (c) about 20 to about 35 wt % butyl paraben;
   (d) about 10 to about 25 wt % citric acid;
   (e) about 0.1 to about 0.25 wt % copper phthalocyanine; and
   (f) about 4 to about 5 wt % ethylene diamine tetraacetic acid; and
   (g) about 2 to about 3 wt % polyethylene oxide; and
 (D) a duck bill check valve within said sleeve at said upper end for impeding the flow of fluid out of said accessory and into said urinary catheter.

* * * * *